United States Patent [19]

Akhtar et al.

[11] Patent Number: 4,950,485

[45] Date of Patent: Aug. 21, 1990

[54] HAIR RELAXER CREAM

[75] Inventors: Muhammad Akhtar, Bolingbrook; Florine Newell, Chicago, both of Ill.

[73] Assignee: Johnson Products Co., Inc., Chicago, Ill.

[21] Appl. No.: 399,385

[22] Filed: Aug. 25, 1989

Related U.S. Application Data

[63] Continuation of Ser. No. 173,318, Mar. 25, 1988.

[51] Int. Cl.$^5$ ............................................. A45D 7/04
[52] U.S. Cl. ...................................... 424/71; 424/70; 132/202; 132/203
[58] Field of Search .................... 424/70, 71; 132/202, 132/203, 204

[56] References Cited

U.S. PATENT DOCUMENTS

| | | | |
|---|---|---|---|
| 3,017,328 | 1/1962 | Childrey et al. | 167/87.1 |
| 4,175,572 | 11/1979 | Hsiung et al. | 132/7 |
| 4,237,910 | 12/1980 | Khalil et al. | 132/7 |
| 4,304,244 | 12/1981 | de la Guardia et al. | 132/7 |
| 4,390,033 | 6/1983 | Khalil et al. | 132/7 |
| 4,416,296 | 11/1983 | Meyers | 132/7 |
| 4,524,787 | 6/1985 | Khalil et al. | 424/70 |

FOREIGN PATENT DOCUMENTS 2141454 6/1984 United Kingdom .

OTHER PUBLICATIONS

"Hair Treatment Products Formulary," *Cosm. & Toilet,* 100, 77,82 (Apr.), 1985.
Harris, R., "Hair Relaxing," *Cosm. & Toilet,* 94,51–56 (Apr.) 1979.
Miranol, Inc. Ethnic Formulary, Product Literature, p1, 9 (2/21/85).
Miranol Chemical Company, Inc., Miranol Products for Cosmetics Toiletries, pp. 25–26, (1985).
DeNavarre M., *The Chemistry and Manufacture of Cosmetics,* 2nd Edition, vol. IV, Chap. 59, pp. 1155, 1159, 1165, Continental Press, Orlando, Fla. (1975).
Balsam, et al., *Cosmetics Science and Technology;* Second Edition, vol. 2, Ch. 22, pp. 251264–267, 277 Wiley-Interscience (1972).

*Primary Examiner*—Joseph L. Schofer
*Assistant Examiner*—Jeffrey T. Smith
*Attorney, Agent, or Firm*—Olson & Hierl

[57] ABSTRACT

A highly alkaline, no-base hair relaxer cream composition is disclosed which is phase-stable on ageing. A composition of this invention is a highly alkaline cosmetic cream base that may be use directly as a no-base hair relaxer or as a no-lye cream that may be converted for use as a no-base, no-lye hair relaxer by admixture with an aqueous activator solution. A method for preparing such a phase-stable no-base hair relaxer cream composition is also disclosed.

33 Claims, No Drawings

HAIR RELAXER CREAM

CROSS REFERENCE TO RELATED APPLICATIONS

This application is a continuation of co-pending application Ser. No. 173,318, filed Mar. 25, 1988.

TECHNICAL FIELD

This invention relates to the straightening or relaxing of hair, and in particular to highly alkaline compositions that are phase-stable on ageing.

BACKGROUND ART

Aqueous highly alkaline hair relaxing or straightening compositions are known in the art. These compositions usually have a highly alkaline pH of about 12 to about 14 due to the presence of an alkaline material, such as water-soluble alkali or alkaline earth hydroxide or an organic chemical base such as guanidine, guanidine hydroxide or quaternary ammonium hydroxide.

Modern highly alkaline hair relaxers are preferably of the type commonly called "no-base" hair relaxers. The term "no-base" means that the scalp need not be coated with a protective oleaginous base such as petrolatum, mineral oil and lanolin, before applying the highly alkaline hair relaxer.

One type of no-base hair relaxer formulation contains as the active hair straightening agent an alkali metal hydroxide, typically a caustic base, such as sodium hydroxide or potassium hydroxide. When a relatively low active level of about 1.5 to about 2.5 weight percent of caustic base is used, the protective base is applied only to the hairline to protect the skin around the forehead, ears and neckline. Such no-base formulations preferably have some of the protective oleaginous material emulsified in an aqueous composition, and are supplied in a "single product" kit.

A preferred and more recently developed type of no-base hair relaxer formulation is commonly called a "no-lye" hair relaxer. With a no-base, no-lye relaxer, a protective base need not be applied to the scalp and may not need to be applied to the hairline. The term "no-lye" means that the active hair straightening agent is an organic chemical base instead of caustic base. In commercial practice, the relatively strong organic chemical base, guanidine is usually present in the form of guanidine hydroxide. However, guanidine hydroxide is not generally stable for long periods in aqueous solutions. Consequently, it must be prepared fresh just before using.

Guanidine hydroxide is generally prepared by reacting an inorganic chemical base such as an alkaline earth hydroxide with an aqueous solution of a salt of the strong organic chemical base guanidine where the anion of this salt is capable of being precipitated by the cation of the alkaline earth hydroxide. In commercially available products of this type, the guanidine hydroxide is generally prepared using guanidine carbonate and calcium hydroxide.

When such a no-lye hair relaxer is commercially used, the product is supplied as a two-part kit. One part contains the guanidine carbonate in substantially liquid form and is commonly called the "activator." The other part contains relatively high amounts of about 4 to about 7 percent calcium hydroxide emulsified in a cosmetic cream base. Prior to using, the consumer or beautician mixes the cream and activator portions of the kit together. The resulting no-lye hair relaxer is then relatively promptly (preferably within 24 hours) applied to the hair.

For convenience, the term "no-lye cream base" as used herein means the cosmetic cream base portion of the foregoing kit containing alkaline earth hydroxide. The term "activator" means the substantially liquid portion of the kit containing the organic chemical base, and the "no-lye hair relaxer" means the resulting admixture of the foregoing no-lye cream base and activator. The term "no-base hair relaxer cream," refers generally to a highly alkaline hair straightening product whether supplied as a single product or as a two-product kit.

Some great strides have been made in formulating highly alkaline no-base hair relaxer compositions, such that proper hair shaft penetration by the active alkaline material is achieved along with minimal scalp injury to thereby improve safety. Also by the incorporation of conditioning agents, the straightened hair has a better feel after such a treatment. However, highly alkaline emulsion products are difficult to compound, require much care during preparation on a commercial scale, and separate or de-emulsify relatively quickly on ageing thereby limiting their commercially useful lifetime.

Most no-base cream products are preferably aqueous emulsions in which water is the continuous phase, i.e., oil-in-water emulsions, because they are easier to rinse from the hair. Instability or de-emulsification therefore results in a destabilized cream product having two distinctly visible phases.

While such destabilized products may be used, they must be remixed before using in an attempt to assure the user that the active ingredients are at the proper levels in the portion being used. However, such mixing, even though done thoroughly by hand, does not, in fact, give the user consistent results with such products. Improper mixing can also cause skin irritation or result in increased hair breakage. Product destabilization and resulting consumer dissatisfaction are among the chief complaints in the industry.

The term "phase-stable" cream refers to an emulsion composition that shows substantially no visible separation into distinct phases on ageing. Thus, phase stability refers to physical stability and is not intended to refer to the chemical stability of the non-alkaline individual ingredients against decomposition by or interaction with the alkaline material under highly alkaline conditions over a relatively long lifetime.

Problems of instability are also caused by the presence of relatively high amounts of water-insoluble oleaginous ingredients that must be co-emulsified with the alkaline material. Oleaginous materials, such as petrolatum and lanolin are desirable in no-lye cosmetic cream bases to maintain the benefits of a no-base procedure. But their water-insoluble character greatly decreases the chances of successfully formulating a phase-stable cream. These problems are magnified when a formula is scaled up for the production of commercial quantities.

Part of the foregoing problems were overcome in U.S. Pat. Nos. 4,390,033 ('033) and 4,237,910 ('910), both to our assignee, by the use of certain lipophilic organically-modified hectorite clay gellants. The disclosures of the '033 and '910 patents are incorporated herein by reference. Those clay gellants were disclosed for stabilizing highly alkaline no-base hair relaxer compositions containing relatively high amounts of oleaginous material against phase separation. Commercial hair relaxer products embodying the principles disclosed in these patents have been marketed.

However, compounding a phase-stable cream, even with the above disclosed hectorite clay gellant, requires considerable care to substantially uniformly disperse the disclosed hectorite clay gellant. In addition, relatively high amounts (about 8 to about 12 weight percent) of the hectorite clay gellant are generally required to achieve a relatively stiff viscous cream. For example, the '033 and '910 patents disclose that at below about 2 weight percent of the hectorite clay gellant, little phase stability improvement was noted and the resulting creams were relatively soft. Thus, while generally elegant relatively stiff viscous creams can be obtained by practicing the emulsion stabilizing principles taught in the '033 and '910 patents, the products are relatively costly to manufacture commercially from the standpoints of costs for labor, materials and energy.

No-base hair relaxers are desirably formulated as emulsified viscous creams so that once applied to the user's hair, they will not drip onto the skin or into the eyes of the person receiving a hair straightening procedure. The cosmetic cream base portion of a no-lye hair relaxer must also mix easily with the activator solution without thinning to a soft runny cream. Additionally, an ideal no-base hair relaxer cream must be easy to remove from the hair at the end of the straightening or relaxer procedure.

The present invention provides such a phase stable cosmetic cream base for use in no-base hair relaxer cream in which many of the above drawbacks in cost are substantially lessened or obviated while retaining the ease of use benefits.

SUMMARY OF THE INVENTION

A highly alkaline cosmetic cream base that is phase stable on ageing is disclosed. The disclosed cosmetic cream base can be prepared to be directly usable as a no-base hair relaxer. Alternatively, a cosmetic cream base of this invention can be prepared as a no-lye cream base convertible for use as a no-base, no-lye hair relaxer by admixing it with an aqueous activator solution. Thus, a highly alkaline cosmetic cream base of this invention can contain all or a part of the alkaline hair relaxing agent.

A cosmetic cream base of this invention is prepared as an aqueous oil-in-water emulsion. A sufficient amount of non-volatile alkaline material dissolved in the continuous water phase provides a pH of about 12 to about 14 in the final hair relaxer and provides all or a portion of the hair-relaxing agent.

Surprisingly, useful stiff, viscous creams are achieved with relatively low amounts of non-water components, based on the total weight of the composition calculated on a dry solids basis. More surprisingly, such creams that are phase-stable on ageing can be prepared at amounts of the phase-stabilizing hectorite clay gellants taught in the '033 and '910 patents discussed earlier that ordinarily produced relatively soft creams with little stability improvement. Further surprisingly, substantially stiff, viscous phase-stable creams are achieved by practicing the principles of this invention even in the absence of the foregoing clay gellants.

The term "phase-stable", as used herein, means that on ageing the emulsion does not de-emulsify, i.e., substantially no separation of the emulsion into distinct phases is visible over a relatively long commercially useful lifetime in the container or jar. The term "commercially useful lifetime" means that no separation of the emulsion into distinct phases is visible after storage for at least about one week upon accelerated ageing at an elevated temperature of about 45 degrees C. (about 113 degrees F.) or for at least about four weeks at ambient room temperature and preferably at least about 3 months.

Briefly described, the non-water components in a cosmetic cream base composition of this invention comprise, exclusive of the alkaline material, a lipophilic oleaginous material, a primary emulsifier that is a nonionic emulsifier comprising a mixture of fatty alcohols having about 12 to about 24 carbon atoms in the fatty carbon chain; an auxiliary emulsifier comprising a hydrophilic nonionic emulsifier, an anionic emulsifier, and an amphoteric or zwitterionic emulsifier; and a polyhydroxy compound having about 3 to about 6 carbon atoms. Additionally, non-water components can include a polymeric conditioning agent and a lipophilic modified hectorite clay gellant of the type disclosed in the '033 and '910 patents.

The total amount of non-water components together with the alkaline material preferably make up no more than about 50 weight percent on a dry solids basis of the total weight of the composition. An emulsified cream-based composition prepared according to the principles of this invention is stable against phase separation over a commercially useful lifetime as defined above.

Reference to weight percent throughout this specification is based on the dry solids weight percent of the individual ingredient present with reference to the total weight of the cream composition.

The alkaline material is selected from the group consisting of water-soluble alkali metal hydroxide or alkaline earth hydroxide. In one embodiment, the alkaline material is the sole hair relaxing agent, so the cosmetic cream base is directly usable as a no-base hair relaxer. For this purpose, the alkaline material is preferably sodium hydroxide present at about 1.5 to about 2.5 weight percent.

In another embodiment, the alkaline material provides part of the hair relaxing agent and is convertible to a no-base no-lye hair relaxer. For this purpose, an alkaline earth hydroxide, preferably calcium hydroxide, is present at about 0.1 to about 10 weight percent to provide a no-lye cream base that is subsequently admixed with an aqueous activator solution. The term "activator" means a solution containing the salt of a relatively strong organic base with an anion capable of being precipitated by the ion of the alkaline earth under alkaline conditions.

A preferred highly alkaline, phase-stable cosmetic cream base of this invention comprises a continuous aqueous phase, a non-volatile alkaline material present at an amount of about 0.1 to about 10 weight percent; about 15 to about 35 weight percent of an oleaginous material, about 3 to about 15 weight percent of a nonionic primary emulsifier comprised as described above; about 0.05 to about 10 weight percent of an auxiliary emulsifying agent comprising a hydrophilic nonionic emulsifier, an anionic emulsifier and an amphoteric or zwitterionic emulsifier that becomes anionic at alkaline pH; zero to about 5 weight percent of a polymeric quaternary nitrogen conditioning agent; about 0.1 to about 10 weight percent of a water-soluble polyhydroxy compound having about 3 to about 6 carbon atoms and zero to about 3 weight percent of a lipophilic-modified hectorite clay gellant.

In one aspect, the method of preparing a stable no-lye cosmetic cream base of this invention comprises mixing and heating together a substantially anhydrous mixture of the oleaginous material, the primary nonionic emulsifying agent, an auxiliary anionic emulsifying agent and, if present, the lipophilic-modified hectorite clay gellant at a temperature of about 80 degrees C. (about 176 degrees F.) for about 30 minutes to form the oil phase of the composition. Water, the remaining emulsifiers and the alkaline material are mixed and heated to about 80 degrees C. for about 15 minutes to form the water phase of the composition. The water phase is then slowly admixed with the oil phase to form an oil-in-water emulsion. After continued mixing and maintenance of the temperature of the resulting emulsion at about 80 degrees C. for about 30 to about 45 minutes, a uniform smooth cream is formed. The cream composition is then force cooled to about 25 degrees C. (about 77 degrees F.). If desired, perfume can be added to the cooling cream composition at between about 55 to about 45 degrees C. (about 131 to about 113 degrees F.). The cooled cream can then be homogenized, if desired, and packaged.

A particularly preferred no-lye cream base prepared by the foregoing method comprises, in the water phase, about 4 to about 7 weight percent of calcium hydroxide; about 0.1 to about 2 weight percent stearoamphoglycinate; about 1 to about 3 weight percent polyoxyethylene (75) lanolin; about 3 to about 8 weight percent propylene glycol and 0.05 to about 5 weight percent of a quaternary homopolymer prepared by polymerizing a diallyldimethylammonium salt. The oil phase comprises about 25 to about 30 weight percent of oleaginous material comprised of a petrolatum-mineral oil mixture containing at least about 50 weight percent petrolatum, about 6 to about 10 weight percent emulsifying wax prepared from a mixture of lipophilic fatty alcohols predominantly having from about 14 to about 22 carbon atoms in the fatty chain, about 0.1 to about 0.5 weight percent of polyoxyethylene (3) ether phosphate, and zero to up to about 2 weight percent of a lipophilic-modified hectorite clay gellant.

The foregoing no-lye cream base is preferably converted to a no-base hair relaxer by admixing it at about 3.5 to about 6 parts by weight with one part by weight of activator solution comprising about 25 to about 30 weight percent guanidine carbonate in a thickened vehicle containing a polyhydroxy compound having 3 to about 6 carbon atoms.

One benefit of a phase-stable cosmetic cream base prepared according to the principles of this invention is that problems leading to skin irritation and uneven hair relaxation due to inconsistent distribution of actives are substantially overcome. A particular advantage is that the cream portion of a no-lye hair relaxer containing relatively high amounts of high calcium hydroxide can be economically and easily prepared on a commercial scale. Another advantage is that no-base hair relaxer creams embodying the principles of this invention display desirable relatively long-term shelf stability on ageing.

Still further advantages and benefits will be apparent to those skilled in the art from the description, examples and claims which follow.

DETAILED DESCRIPTION OF THE INVENTION

It has now been found that aqueous highly alkaline cosmetic cream base compositions can be formed which are phase-stable on ageing for a commercially useful lifetime. The term "highly alkaline", as used herein, refers to a pH from about 12 to about 14, preferably to a pH from about 12 to about 13. This pH is achieved by the presence of an alkaline material that is sufficiently water-soluble in the continuous water phase to provide a highly alkaline pH.

The term "phase-stable" as described above refers to the physical stability of the emulsified composition. As stated earlier, phase-stable compositions defined herein are cosmetic cream bases that are relatively stiff viscous creams which do not visibly de-emulsify or separate on ageing at ambient temperature for at least about four weeks or at about 45 degrees C. (about 113 degrees F.) for at least about 1 week. For purposes of illustrating this invention, the foregoing time period is considered indicative of a commercially useful lifetime in the field.

In actual practice, however, it has been surprisingly found that compositions prepared according to this invention containing relatively low amounts of non-water components remain phase-stable for at least about 3 to about 6 months, both at ambient room temperature and at elevated temperatures. These compositions thereby provide products having concentrations of active ingredients that are substantially constant throughout their useful lifetimes.

The term "non-water components" refers to all ingredients, other than water. A "relatively low amount" means that the emulsion-forming ingredients and the alkaline material present as part or all of the hair-relaxing agent together make up no more than about 50 weight percent on a dry solids basis of the total cream composition. A "relatively stiff viscous cream" as used herein defines a product having a Brookfield viscosity of about 100,000 to greater than about 900,000 centipoise (cps), as measured with a model RVT Helipath spindle No. TE rotating at 5 revolutions per minute (rpm) for one minute at about 25 degrees C. (about 77 degrees F.).

A no-base, no-lye hair relaxer preferably contains as the hair-relaxing agent, a water-soluble alkaline caustic material that is preferably a strong organic base, such as guanidine hydroxide. This alkaline material is made just before application of the composition to the hair by the reaction of guanidine carbonate with calcium hydroxide. In this embodiment, calcium hydroxide is present in the emulsified no-lye cream base, and guanidine carbonate, in a separate aqueous activator solution, is combined with the emulsion just before use. Alternatively, the guanidine carbonate may be included in the emulsion and calcium hydroxide is added just before use in an aqueous suspension. Other alkaline earth hydroxides, such as barium or strontium hydroxide may be used in place of calcium hydroxide to release free guanidine from guanidine carbonate. Alkaline earth oxides may also be used, producing hydroxides when added to water.

The amount of guanidine in the final composition is from about 0.05 to 0.8 molar, preferably from about 0.4 to 0.6 molar. Guanidine concentrations within this range are obtained from guanidine carbonate concentrations in the final mixture between about 0.031 and 0.38 molar and calcium hydroxide concentrations in the final mixture between about 0.025 and 2.2 molar. In the emulsified composition prior to the addition of aqueous guanidine carbonate, the amount of calcium hydroxide is generally between about 0.1 and 10 weight percent, and preferably between about 4 and 7 weight percent.

Other organic bases that may be used in place of guanidine, include N-methyl guanidine, dimethylaminoguanidine (sym. and asym.), acetamidine, dimethylaminoamidine, aminoamidine and acetamide. The organic base may be liberated from salts other than the carbonate salt, such as from a sulfate or sulfite salt. In general, the emulsified composition may contain a water soluble salt of a strong organic base with an anion capable of being precipitated by an alkaline earth metal ion under alkaline conditions.

Alternatively, a cosmetic cream base for use directly as a no-base hair relaxing composition can contain a water-soluble alkaline caustic material which is capable of both bringing the pH of the composition to a value of about 12 to about 14, and acting as the sole hair relaxing agent. Alkali metal hydroxides, including sodium hydroxide, potassium hydroxide and lithium hydroxide may be used as the water-soluble alkaline caustic material. Sodium hydroxide is preferred and may be present in amounts from about 1 to about 3 weight percent of the total composition, preferably from about 1.5 to about 2.5 weight percent.

In the case of a no-base, no-lye cream base, the physical stability of the cream portion of the product does not interfere with the formation of the active hair relaxing agent when the no-lye cream base is admixed with the activator portion. For example, guanidine hydroxide can be formed in an admixture of a phase-stable cosmetic cream base containing calcium hydroxide and an activator containing guanidine carbonate. However, the stability of the phase-stable cosmetic cream base may eventually be overcome in the admixture by the presence of the free organic base, such as guanidine or guanidine hydroxide. Thus, a phase-stable no-lye cosmetic cream base convertible for use in a hair relaxer is supplied in a separate container than the activator for a two-part hair relaxer kit.

In compounding a cream base of this invention the oil phase is comprised of the substantially anhydrous, lipophilic ingredients. These generally include the oleaginous material, the primary nonionic emulsifier and an anionic emulsifier.

About 15 to about 35 percent of the highly alkaline cosmetic cream base compositions of this invention are comprised of lipophilic oleaginous material. The oleaginous material predominantly includes petrolatum, mineral oils and mineral jellies, but can also include lanolin, and like unctuous emulsifiable materials. Particularly preferred is a petrolatum-mineral oil mixture where the petrolatum comprises at least about 50 weight percent, preferably between about 55 and about 65 weight percent, of the weight of the mixture.

Useful petrolatum is available in several grades based upon both viscosity, melting point and color. The Saybolt seconds universal viscosities (S.S.U) of these products range from between about 50 and about 90 (50/90) S.S.U. at 210 degrees F. Preferably, a colorless or "white" product having a Saybolt viscosity of about 55/75 S.S.U. at 210 degrees F. and melting points in the degree range of 135/140 F. and 127/137 F. are used. Preferably, a grade that meets the standards of the United States Pharmacopeia (U.S.P.) is used.

Mineral oils useful herein are preferably U.S.P. grade white oils. Preferably, a colorless or "white" oil is used having Saybolt viscosities at 100 degrees F. of about 50/350 S.S.U. and specific gravities at 77 degrees F. of about 0.822 to about 0.895 (0.822/0.895). The materials having Saybolt viscosities of about 50/60 S.S.U. at 100 degrees F. and specific gravities in the ranges 0.822/0.833 at 77 degrees F. are preferred.

In addition, a mineral jelly compounded of white petrolatum, white mineral oil and wax may also be used as an oleaginous material in the compositions of this invention.

The oleaginous materials may be present at about 15 to about 35 weight percent, preferably at about 25 to about 30 weight percent. However, the percentage actually used in a product depends upon the desired product consistency. For example, where a no-lye cream base is desired, the consistency of the cream must permit it to be admixed with a liquid activator. The resulting admixture must produce a no-base hair-relaxer cream that is substantially free of lumps and that does not thin to a runny soft product.

For a no-lye cream base composition, the oleaginous material preferably comprises a petrolatum-mineral oil mixture containing at least about 50 weight percent petrolatum and present at about 25 to about 30 weight percent of the total weight of the no-lye cream base.

The oleaginous material can include lipophilic-modified hectorite clay gellants. It has been surprisingly found, however, that unlike prior compositions, phase-stable, relatively stiff creams can be prepared with relatively low amounts of up to about 3 weight percent, preferably of up to about 2 weight percent, of these clay gellants.

Where present, lipophilic hectorite clay gellants are those comprised of hectorite clays modified with (1) a quaternary nitrogen-containing compound such as stearalkonium chloride or quaternium-18 which contains at least one long chain substituent having about 8 to about 20 carbon atoms on the quaternary nitrogen atoms, (2) propylene carbonate, and (3) a non-polar organic liquid. Examples of such non-polar organic liquids include but are not limited to mineral spirits, mineral oil, glycerides, such as castor oil, a mixture of lanolin oil and isopropyl palmitate, and the like. [Stearalkonium chloride and quaternium-18 are defined in the CTFA Cosmetic Ingredient Dictionary, 3rd ed., published in 1982 by The Cosmetic Toiletry and Fragrance Association, Inc., at pages 299 and 267, respectively.]

Specific, useful lipophilic gellants which are commercially available as mastergels include: Bentone Gel MIO, comprised of mineral oil, propylene carbonate and quaterium-18 hectorite; Bentone Gel CAO, comprised of propylene carbonate, castor oil and stearalkonium hectorite; Bentone Gels SS71 and S130, comprised of mineral spirits (ligroin or petroleum spirits having a boiling range of about 318 degrees–400 degrees F.), propylene carbonate and quaternium-18 hectorite; and Bentone Gel Lantrol, comprised of propylene carbonate, a mixture of lanolin oil (dewaxed lanolin) and isopropyl palmitate, and stearalkonium hectorite. The above hectorite gellants may be individually used, may be interchanged, one for the other in a given composition, or may be mixed together in a composition.

The lipophilic-modified hectorites may be present in the no-lye cream base portion of a no-base hair relaxer of this invention from zero to up to about 3 weight percent, preferably up to about 2 weight percent, of the total composition prior to admixture with activator.

Nonionic emulsifying agents useful as the primary emulsifier, are preferably emulsifying waxes that meet the standards of the National Formulary (N.F.) or British Pharmacopeia (B.P.) and can either be the non-self-emulsifying or the self-emulsifying type. The term "emulsifying wax" denotes solid nonionic emulsifiers known in the art that are prepared as a mixture of fatty alcohols having from about 12 to about 24 carbon atoms, preferably predominantly lipophilic fatty alcohols having from about 14 to about 20 carbon atoms. Self-emulsifying waxes are typically prepared with an auxiliary hydrophilic emulsifier present. The hydrophilic nonionic emulsifiers present in the primary nonionic emulsifier as part of the emulsifying wax are usually polyoxyethylene derivatives of fatty acid esters of sorbitol and sorbitol anhydride. Preferred are polysorbates which generally comprise mixtures of oleate or stearate esters condensed with ethylene oxide.

A preferred N.F. grade emulsifying wax is prepared from cetostearyl alcohol containing a polyoxyethylene derivative of a fatty acid ester of sorbitan. This material is known as Emulsifying Wax N.F. and is a creamy white, wax-like solid which is freely soluble in ether, chloroform, alcohol and most hydrocarbon solvents, but is insoluble in water. It melts at a temperature between 48 degrees and 52 degrees C., has a hydroxyl value between 178 and 192, an iodine value not more than 3.5, a saponification value not more than 14, and a pH (in a dispersion of 3 parts in 100 parts of water) between 5.5 and 7.0. Emulsifying Wax N.F. is commercially available from a number of suppliers. Exemplary and preferred materials are sold under the name POLAWAX by Croda, Inc., New York, New York; and LIPOWAX P by Lipo Chemicals, Inc., Paterson, New Jersey.

Other useful emulsifying waxes are commercially sold comprising balanced blends of lipophilic fatty alcohols (some distilled or double distilled) derived from fatty acids containing about 12 to about 24 carbon atoms and ethylene adducts thereof. Particularly preferred are emulsifying waxes containing about 14 to about 20 carbon atoms, more preferably about 16 to about 18 carbon atoms. Alternatively, the primary nonionic emulsifier can be a balanced blend of the individual lipophilic fatty alcohols, having about 14 to about 20 carbon atoms, more preferably about 16 to about 18 carbon atoms. Particularly useful fatty alcohols include cetyl alcohol, stearyl alcohol, tallow fatty alcohols and like saturated monovalent linear alcohols obtained from vegetable sources, animal oils and fats.

Particularly preferred are tallow fatty alcohols manufactured and sold under the trademark HYDRENOL D or DD by Henkel KGaA, Germany. According to the manufacturer, these materials comprise zero-2 percent $C_{12}$; 3-7 percent $C_{14}$; 25-35 $C_{16}$; 60-70 percent $C_{18}$; and zero to 2 percent $C_{20}$ moieties; less than 1.2 percent hydrocarbons, less than 0.3 percent water; and has an acid value of less than 0.1; a saponification value of less than 1.2; an iodine value of less than 1; a hydroxyl value of 210-220; and solidifies in the range of 48-52 degrees C. Another preferred nonionic emulsifier is a fatty alcohol mixture containing cetyl and stearyl alcohols sold under the trademark TA1618F by The Procter & Gamble Company Industrial Chemicals Divisions, Cincinnati, Ohio.

In the practice of this invention, the primary nonionic emulsifying agent is generally present at about 3 to about 15 weight percent, preferably at about 5 to about 12, more preferably at about 6 to about 10.

Anionic emulsifiers may be illustrated by polyoxyethylene oleyl ether phosphates having about 3 to about 20 oxyethylene groups, sodium lauryl sulfate, and the stearic acid anion and the like. Polyoxyethylene (3) oleyl ether phosphate is particularly preferred. In compounding a phase-stable cream, an anionic emulsifier in substantially non-aqueous form is included in the oil phase at about 0.01 to about 1.0 weight percent, preferably at about 0.1 to about 0.5 weight percent of the total composition.

The water phase of the cream composition generally contains the relatively more water-soluble auxiliary emulsifiers, amphoteric or zwitterionic emulsifiers and hydrophilic nonionic emulsifiers as well as a polyhydroxy compound having about 3 to about 6 carbon atoms, and polymeric conditioning agent, where present. Amphoteric or zwitterionic emulsifiers that become anionic at alkaline pH are preferred. A zwitterionic emulsifier contains both cationic and anionic moieties in the same molecule and includes amphoteric surface active agents.

Suitable amphoteric surfactants include alkylamphocarboxyproprionates, and alkylamphoglycinates having mono- or di-carboxyl groups derived from fatty acids having about 10 to about 22 carbon atoms in the fatty alkyl chain. Particularly preferred is stearoamphoglycinate, the CTFA name for 2-heptadecyl-1-carboxymethyl-1-(2-hydroxyethyl)-2-imidazolinium chloride, sold under the tradename Miranol DM by the Miranol Chemical Company, Inc. Additional amphoteric or zwitterionic emulsifiers include the class of surface active agents having an aminopropionate structure, such as N-fatty alkyl beta propionic acid and alkali metal salts thereof. Commercial materials having lauryl, myristyl, coco and tallow fatty alkyl groups are sold commercially under the tradename DERIPHAT by General Mills Chemicals, Inc., Cosmedia Group, Minneapolis, Minnesota.

Amphoteric emulsifier can be present at about 0.01 to about 2 weight percent, preferably at about 0.1 to about 1, more preferably at about 0.2 to about 0.5 weight percent, dry solids basis.

Hydrophilic nonionic emulsifiers include polyoxyethylene derivatives of fatty acid esters of sorbitol and sorbitol anhydride; polyethylene glycol esters of fatty acids, polyoxyethylene ethers of fatty alcohols, polyethylene oxide-polypropylene oxide condensates and polyoxyethylene lanolin ethers, and the like. Particularly preferred is polyoxyethylene (75) lanolin.

Hydrophilic nonionic emulsifiers can be present at about 0.01 to about 8 weight percent preferably at about 0.5 to about 5 weight percent, more preferably at about 1 to about 3 weight percent.

The use of particular concentrations of the auxiliary emulsifiers can be varied as desired to keep the make up of the total of the non-components together, with the alkaline material at no more than about 50 weight percent of the total composition. It has been found beneficial to use about 0.05 to about 10 weight percent of auxiliary emulsifier, inclusive of the anionic emulsifier.

In a preferred composition where about 0.01 to about 1 weight percent anionic emulsifier is present in the oil phase, the auxiliary emulsifier can comprise up to about 9 weight percent of a mixture of a hydrophilic nonionic emulsifier, preferably polyoxyethylene (75) lanolin, and an amphoteric or zwitterionic emulsifier in the water phase, preferably stearoamphoglycinate.

Suitable polyhydroxy compounds include propylene glycol, glycerin, butylene glycol, hexylene glycol, sorbitol and the like. Particularly preferred is propylene glycol. The polyhydroxy compounds can be present at about 0.1 to about 10 weight percent, preferably at about 3 to about 8 weight percent. Sorbitol is generally preferred as a component of the activator solution for a no-lye hair relaxer.

When present, the polymeric conditioning agent is preferably a quaternary nitrogen polymer prepared by polymerizing a diallyldimethylammonium salt. Details concerning the preparation of this material can be found in U.S. Pat. Nos. 3,288,770 and 3,412,019. This cationic polymer is present at about 0.05 to about 5 weight percent, more preferably at about 0.1 to about 2 weight percent.

Homopolymers and copolymers of polydiallyldimethylammonium chloride are available in aqueous compositions sold under the trademark MERQUAT by E. M. Merck & Co. The homopolymer that is named polyquaternium-6 in the CTFA Dictionary and is trademarked MERQUAT-100 is particularly preferred. However, a copolymer reaction product of dimethyldiallylammonium chloride with acrylamide monomers, named polyquaternium-7 in the CTFA Dictionary and sold under the trademark MERQUAT-550 can also be used. It is understood that a number of other cationic polymeric conditioning agents are commercially available and known that can also be used, the disclosure of the preferred cationic polymer is not intended to limit the scope of this invention.

The hair relaxer composition can also include cosmetic adjuvants, such as auxiliary emollients, auxiliary thickening agents, perfumes, preservatives, and product colorants present in the cosmetic cream base composition, in the activator, or in both.

To prepare a highly alkaline cosmetic cream base composition of this invention, a relatively easy method using inversion emulsification methods is used. As practiced, the substantially anhydrous components of the oil phase are mixed together, including the hectorite clay gellant when present, by heating and agitating the mixture at about 80 degrees C. (about 113 degrees F.) for about 30 minutes or until a substantially homogeneous uniform dispersion results.

In a separate vessel, the remaining non-water components, except sodium hydroxide when present, are mixed with water to form the water phase. This mixture is heated and agitated at about 80 degrees C. for about 15 minutes or until a substantially uniform solution results.

The bulk portion of the water phase is then slowly added with agitation to the oil phase at a rate sufficient to effect inversion to oil-in-water emulsion. Agitation is continued thereafter for about 30 to about 45 minutes. The agitated mixture is then cooled to between about 50 to about 45 degrees C. (about 122 and 113 degrees F.) at which temperature aqueous (50 weight percent solution) sodium hydroxide, adjuvants, perfume and the like, if present, are added. The mixture is diluted to its final volume with deionized water if necessary. The mixture is then stirred, as necessary, for about an additional 15 minutes to ensure homogeneity, or until a relatively stiff viscous cream base results. The cream is then force cooled to about ambient temperature (about 25 degrees C. or about 72 degrees F.). On reaching ambient temperature, the mixture can be homogenized by conventional techniques, such as by ultrasonic mixing.

In another method aspect, the polyhydroxy compound can be withheld from the water phase initially and added to the heated admixture of water and oil phase instead.

The preparation of no-base hair relaxer creams in which sodium hydroxide is the active hair-relaxing agent, is generally similar to that of a no-lye cream base, except for withholding the inclusion of the sodium hydroxide until the emulsion is formed and cooled to between about 50 and about 45 degrees.

Cosmetic cream bases, especially no-lye cream bases, prepared according to the above procedures surprisingly are stiff viscous creams having a Brookfield viscosity of at least about 100,000 to greater than about 900,000 cps. Preferably, the viscosity is in a range of between about 150,000 to about 800,000, more preferably between about 200,000 to about 600,000. The creams maintain their viscosity even on accelerated ageing at about 45 degrees C. (about 113 degrees F.) as well as at ambient room temperature for as long as about 3 to about 6 months.

When guanidine is the water-soluble alkali hair-relaxing agent and the emulsified cream composition contains calcium hydroxide, or another alkaline earth hydroxide, it is necessary to blend the emulsified composition, just before application to the hair, with an activator solution. The activator comprises an aqueous solution of about 25 to about 30 weight percent guanidine carbonate, preferably containing a small amount of a polyhydroxy compound and a thickener. The emulsified compositions are blended in proportions producing free guanidine or guanidine hydroxide in an amount within the limits disclosed above.

It has been surprisingly found that an admixture comprised of about 3.5 to about 6 parts of a "no-lye" cosmetic cream base of this invention with one part of activator provides improved hair straightening where the aqueous activator solution comprises guanidine carbonate at about 28 to about 30 weight percent, preferably about 29 weight percent, prior to admixture. The reason for the improved hair straightening effect is not fully understood.

Particularly preferred in this regard, is an activator including sorbitol at about 0.2 to about 0.5 weight percent, dry solids basis and a natural gum thickening agent at about 0.1 to about 0.3 weight percent.

When using the stable cosmetic cream bases of this invention in a no-base hair relaxers procedure, it is preferable that the person on whose head the compositions will be used (the model) not wash her (or his) hair for at least 24 hours prior to the relaxer treatment. This preference stems from the scalp protecting effect produced by the model's own sebum secretions. In addition, while washing the hair, slight physical damage can occur to the scalp which can become aggravated by the alkaline material in the relaxer.

The model's hair is divided into four portions as delineated by the areas separated when hypothetical lines are drawn from ear-to-ear and from nose-to-backbone. Starting with the rear portions, the relaxer cream is applied to the hair with the back or smooth side of a comb (opposite from the teeth). Care is taken to avoid putting the composition on the scalp and about $\frac{1}{8}$-$\frac{1}{4}$ inch of the root end (lower portion) of the hair shaft. This process takes about 8 minutes for treatment of all the model's hair.

Each portion of the hair is then physically smoothed with the comb back. At this time in the treatment, the scalp and lower portions of the hair shafts are contacted with the relaxer cream. The smoothing step helps to ensure adequate hair shaft penetration and softening by the relaxer and also puts tension on the hair to help in straightening the hair. The smoothing step is then repeated to facilitate straightening. The total time for smoothing (both the initial and the repeat steps) normally takes from about 5 to about 10 minutes, depending upon the hair length and thickness. Thus, at this point, the relaxer is on the head for about 13 to about 18 minutes.

The relaxer is then thoroughly and rapidly removed from the hair by rinsing with water having a temperature of about 37 degrees C. (about 77 degrees F.). The rinsing step is followed by a shampooing with a non-alkaline shampoo. The shampoo is preferably buffered on the acid side of neutral at about pH 4 to 6 so that residual alkali left in the hair or on the scalp is neutralized. This shampooing is usually repeated two to three times.

After shampooing, the hair may be treated with a conditioner to improve wet combing and hair feel. When the conditioning relaxers of this invention are used, no extra conditioning step is needed. The hair may then be set and dried in a desired coiffure as is known in the art.

In effect, the highly alkaline no-lye cosmetic cream base compositions of this invention are of high water, low solids type. The following Examples illustrate cream bases of this invention with generally preferred ingredients and methods of preparation, but are not intended to be limited thereby.

EXAMPLE 1

Phase Stable No-Lye Cream Base

The following compositions illustrate no-lye cream base compositions containing low amounts of clay gellant convertible for use as a guanidine based no-base hair relaxer by admixture with activator.

| Components | Weight Percent, Dry Solid Basis of Emulsified Cream Base | | | | | |
|---|---|---|---|---|---|---|
| | A | B | C | D | E | F |
| I. Oil Phase | | | | | | |
| Petrolatum (Note 1) | 15 | 15 | 15 | 15 | 15 | 15 |
| Mineral Oil (Note 2) | 12 | 10 | 12 | 10 | 10 | 12 |
| Emulsifying Wax N.F. (Note 3) | 8 | 9 | 8 | 7 | 9 | 9 |
| Polyoxyethylene (3) Oleylether phosphate | 0.25 | 0.25 | 0.25 | 0.25 | 0.25 | 0.25 |
| Modified Hectorite Clay Gellant (Note 4) | 2 | 2 | 2 | 2 | 2 | 1.5 |
| II. Water Phase | | | | | | |
| Water, deionized to 100 percent | Q.S. | Q.S. | Q.S. | Q.S. | Q.S. | Q.S. |
| Calcium hydroxide | 6.3 | 5 | 5 | 5 | 6 | 6 |
| Polymeric quaternary nitrogen conditioning agent (Note 5) | — | 1.2 | — | 1.2 | 1 | — |
| Amphoteric Emulsifier (Note 6) | 0.37 | 0.37 | 0.37 | 0.37 | 0.5 | 0.25 |
| Polyoxyethylene (75) lanolin (Note 7) | 1.5 | 1.5 | 1.5 | 1.5 | 1.5 | 1.5 |
| Propylene glycol | 5 | 5 | 5 | 5 | 6 | 4 |

-continued

| Components | Weight Percent, Dry Solid Basis of Emulsified Cream Base | | | | | |
|---|---|---|---|---|---|---|
| | A | B | C | D | E | F |
| III. Perfume | — | — | — | Q.S. | — | — |

Note 1. White petrolatum having a melting point of 127/137 degrees F. and a Saybolt viscosity at 210 degrees F. of 60/80 S.U.S. may be used.
Note 2. White mineral oil having a Saybolt viscosity at 100 degrees F. of 50/60 S.S.U. and a specific gravity in the range of 0.822/0.833 at 77 degrees F. may be used.
Note 3. POLAWAX available from Croda, Inc. or LIPOWAX P available from Lipochemical may be used.
Note 4. A modified hectorite clay gellant sold by N.L. Industries, Inc. under the trademarks Bentone Gel MIO, Bentone Gel CAO, Bentone Gel SS71, Bentone Gel S130 and Bentone Gel Lantrol may be used.
Note 5. A water-soluble quaternary nitrogen-containing polymer available from Merck & Co., Inc. under the trademark Merquat 100 as a 40 percent active aqueous solution may be used.
Note 6. Preferably stearoamphoglycinate available from the Miranol Chemical Company, Inc. under the trademark Miranol DM as a 20 percent active aqueous paste.
Note 7. Available as 50 percent active in water under the trademark LANETO 50 from the R.I.T.A. Corporation, Crystal Lake, IL.

The components of the oil phase are placed together in a heatable container equipped with a propeller-type mixer, heated to about 80 degrees C and mixed for about 30 minutes or until a substantially uniform dispersion is formed. In a separate heatable container, the water and remaining components of the water phase are placed and also provided with a mixer. This admixture is heated to about 80 degrees C. and mixed for about 15 minutes.

The water phase is then added slowly with mixing agitation to the oil phase while maintaining the temperature at about 80 degrees C. The resulting emulsion is maintained at this temperature under continued agitation for about 30 to about 45 minutes and is then cooled to between about 55 degrees C. and about 45 degrees C at which point perfume, if present, is added. The emulsion is again mixed for about 15 minutes and allowed to cool to form a substantially smooth cream base at about 45 to about 35 degrees C. and is force cooled to about 25 degrees C. It is then homogenized and packaged.

The cream bases are relatively stiff viscous compositions that do not separate into distinct phases on ageing. For example, Cream Bases A–D had Brookfield viscosities at 25 degrees C. (Model RVT spindle model No. TE at 5 rpm for 1 minute) of about 200,000 to about 350,000 cps. On ageing at ambient room temperature, their viscosities appeared to stabilize at about 350,000 to about 525,000 cps. Typically at about 400,000 to about 480,000 cps.

The phase stability of Cream Base A was followed under accelerated ageing conditions at about 45 degrees C. for at least six months. No separation was observed.

EXAMPLE 2

Phase Stable No-Lye Cream Base

This example illustrates no-lye cream base compositions containing as the primary emulsifier, a mixture of fatty alcohols having about 16 to about 18 carbon atoms ($C_{16}$–$C_{18}$).

| Components | Weight percent, Dry Solid Basis of Emulsified Cream Base | | | |
|---|---|---|---|---|
| | G | H | I | J |
| I. Oil Phase | | | | |
| Petrolatum (Note 1 above) | 15 | 15 | 20 | 15 |
| Mineral Oil (Note 2 above) | 10 | 10 | 14 | 10 |

-continued

| Components | Weight percent, Dry Solid Basis of Emulsified Cream Base | | | |
|---|---|---|---|---|
| | G | H | I | J |
| $C_{16}$-$C_{18}$ Fatty Alcohols (Note 8) | 9 | 9 | 7 | 8 |
| Polyoxyethylene (3) Oleylether phosphate | 0.25 | 0.1 | 0.5 | 0.25 |
| Modified Hectorite Clay Gellant (Note 4 above) | 2 | 2.1 | 0.1 | — |
| II. Water phase | | | | |
| Water, deionized to 100 percent | Q.S. | Q.S. | Q.S. | Q.S. |
| Calcium hydroxide | 6.3 | 6.3 | 4 | 5.5 |
| Polymeric quaternary nitrogen conditioning agent (Note 5 above) | 1.2 | 1.2 | — | 1.2 |
| Amphoteric Emulsifier (Note 6 above) | 0.37 | 0.37 | 0.1 | 0.2 |
| Polyoxyethylene (75) lanolin (Note 7 above) | 1.5 | 1.5 | 1 | 1.5 |
| Propylene glycol) | 5 | 5 | 8 | 5 |
| III. Perfume | Q.S. | — | Q.S. | Q.S. |

Note 8. A fatty alcohol mixture containing cetyl and stearyl alcohols sold under the trademark TA 1618F by Proctor & Gamble or a tallow fatty alcohol sold under the trademark HYDRENOL D by Henkel KGaA, Germany may be used.

The procedure of Example 1 is followed in preparing the compositions and in measuring Brookfield viscosity.

The Brookfield viscosity of Cream Base G was about 280,000 to about 350,000 cps, and that of Cream Base H was about 250,000 to about 400,000 cps. The viscosities of both creams bases stabilized on ageing at ambient temperature at between about 425,000 to about 500,000 within about a week.

EXAMPLE 3

Phase Stable No-Lye Cream Bases

This example illustrates no-lye cream bases that are stabilized using Emulsifying Wax as the primary emulsifier and no hectorite clay gellant, but are otherwise generally prepared following the procedure of Example 1.

| Components | Weight percent, Dry Solid Basis of Emulsified Cream Base | | | | |
|---|---|---|---|---|---|
| | K | L | M | N | O |
| I. Oil Phase | | | | | |
| Petrolatum (Note 1 above) | 15 | 15 | 15 | 15 | 15 |
| Mineral Oil (Note 2 above) | 12 | 12 | 12 | 12 | 12 |
| Emulsifying Wax N.F. | 9 | 8 | 7 | 7 | 9 |
| Polyoxyethylene (3) Oleylether phosphate | 0.25 | 0.25 | 0.25 | 0.25 | 0.25 |
| II. Water phase | | | | | |
| Water, deionized to 100 percent | Q.S. | Q.S. | Q.S. | Q.S. | Q.S. |
| Calcium hydroxide | 5 | 5 | 5 | 5 | 5 |
| Polymeric quaternary nitrogen conditioning agent (Note 5 above) | 1.2 | — | — | 1.2 | — |
| Amphoteric Emulsifier (Note 6 above) | 0.37 | 0.37 | 0.37 | 0.37 | 0.37 |
| Polyoxyethylene (75) lanolin (Note 7 above) | 1.5 | 1.5 | 1.5 | 1.5 | 1.5 |
| Propylene glycol | 5 | 5 | 5 | 5 | 5 |

The Brookfield viscosity of freshly prepared Cream K was about 240,000 cps to about 250,000 cps, increasing to between about 480,000 to about 950,000 cps on ageing at ambient room temperature at about 2 to about 4 weeks.

The Brookfield viscosities of freshly prepared Creams L–O ranged between about 150,000 to about 300,000 cps and between about 350,000 and about 750,000 on ageing at ambient room temperatures for about one week.

EXAMPLE 4

No-Base Hair Relaxer

Cream bases that are directly usable as a no-base hair relaxer can be prepared by substituting about 1 to about 2.5 weight percent sodium hydroxide in the formula for Cream A of Example 1 in place of calcium hydroxide.

In preparing this hair relaxer cream, the procedure of Example 1 is followed, except that the sodium hydroxide is withheld from the water phase. When the cream base has cooled to between about 50 and 45 degrees C., the sodium hydroxide is added, preferably as a concentrated aqueous solution, before the perfume. To ensure homogeneity the cream is stirred about another 15 minutes prior to adding the perfume.

EXAMPLE 5

Phase Stable No-Lye Cream Base

Cream Base G of Example 2 was prepared in a commercial scale quantity following the general procedure of Example 1, except that propylene glycol was initially withheld from the water phase. After the water phase had been added and the heated emulsion reacted about 75 to about 80 degrees C., the propylene glycol was added while maintaining the temperature. A viscous cream base was obtained at between about 40 and about 35 degrees C.

EXAMPLE 6

No-Base No-Lye Hair Relaxer Cream

This example illustrates the conversion of no-lye cream base of this invention for use in a no-base no-lye hair relaxing procedure.

An aqueous activator (X) solution of guanidine carbonate was prepared containing about 28 to about 30 weight percent guanidine carbonate, about 0.2 to about 0.25 weight percent sodium alginate (as thickening agent) about 0.35 weight percent, sorbitol (dry solids basis) and sufficient preservative.

One part of the activator (X) was mixed with about 3.5 to about 3.7 parts of Cream Base G of Example 2 to provide a hair relaxer cream. In commercial practice, a representative admixture of about 220 grams Cream Base G and about 60 g of the foregoing activator (X) containing about 29 weight percent guanidine carbonate was particularly preferred as a hair relaxer cream (HR-A).

Likewise Cream Base A of Example 1 can be converted to a hair relaxer (HR-B) by admixing one part of activator (X) with about 3.7 to about 6 parts Cream Base A to provide a hair relaxer varying from "super" to "regular" strength.

EXAMPLE 7

No-Base No-Lye Hair Relaxer

In salon tests, hair relaxer HR-A of Example 6 gave relaxing or straightening results that were equivalent to or superior to those obtained with a commercial no-base no-lye hair relaxer cream of comparable alkalinity stabilized with relatively high amounts of hectorite clay gellant in accordance with the teachings of U.S. Pat. Nos. 4,390,033 and 4,237,910.

A salon test was made with 50 volunteer persons having medium to coarse curly hair using a half-head comparison method. Each person received a hair relaxer procedure on one side with hair relaxer HR-A of Example 6 and on the opposite side with commercial hair relaxer (C) prepared using activator (X) of Example 6 containing about 29 to about 30 weight percent guanidine admixed with a commercial cream in the same proportions as for HR-A. The hair relaxing procedure was followed applying a commercial neutralizing shampoo, using the same product on both sides.

The hair relaxing or straightening effect of hair relaxer HR-A was judged equivalent. The consistency of hair relaxer HR-A was also judged substantially more viscous than the hair relaxer C. This result was surprising because the commercial cream was phase-stabilized with a relatively high amount of modified hectorite clay gellant in excess of about 12 weight percent and contained substantially the same amount of calcium hydroxide. Additionally, the HR-A cream was equivalent to or preferred over the commercial hair relaxer for ease of distributing and smoothing through the hair, ease of rinsing, after-treatment feel of the wet and dry hair, sheen and manageability.

In another salon test, 52 persons having medium to coarse hair received a no-lye hair relaxer procedure with no-lye hair relaxer HR-A, of Example 6. The product was applied generally following known hair-relaxing procedures described earlier. The results again showed that the consistency of the hair relaxer HR-A, was very workable through the hair, judged not too firm or too soft, gave good relaxation results and made the hair soft, and easy to comb.

In a third salon test, five persons received a hair-relaxer procedure in a half-head comparison between a commercial no-base, no-lye cream and Cream Base H of Example 2. Each no-lye cream was mixed with the commercial activator supplied, which was generally similar to activator (X) of Example 6, and the resulting hair relaxer applied according to the manufacturer's directions.

The results showed that the consistency of the hair relaxer prepared with Cream Base H and its rinsing and after-treatment effect on the hair was substantially equivalent to the commercial product.

The present invention has been described generally and with respect to preferred embodiments. It will be understood that modifications and variations of the disclosed method and compositions may be made without departing from the spirit and scope of the novel concept of the present invention.

What is claimed is:

1. A phase-stable, highly alkaline aqueous composition suitable for use as a cosmetic base for a no-base hair relaxer, the composition comprising an oil-in-water emulsion containing a sufficient amount of a non-volatile inorganic alkaline material selected from the group consisting of water-soluble alkali metal hydroxide and alkaline earth hydroxide dissolved therein to provide a pH of from about 12 to about 14 and non-water components, exclusive of the alkaline material, based on the total weight of the composition, on a dry solids basis, consisting essentially of:

(a) about 15 to about 35 weight percent of a lipophilic oleaginous material including zero to about 2 weight percent of a lipophilic-modified clay gellant;

(b) about 3 to about 15 weight percent of a primary nonionic emulsifier comprising a mixture of fatty alcohols having from about 12 to about 24 carbon atoms in their fatty carbon chain;

(c) about 0.05 to about 10 weight percent of an auxiliary emulsifier comprising a hydrophilic nonionic emulsifier, an anionic emulsifier, and an amphoteric or zwitterionic emulsifier;

(d) zero to about 5 weight percent of a polymeric quaternary nitrogen conditioning agent;

(e) about 0.1 to about 10 weight percent of a water-soluble polyhydroxy compound having 3 to about 6 carbon atoms;

the non-water components (a)–(e) co-emulsified together with the alkaline material making up no more than about 50 weight percent of the total weight of the composition, and all or a portion of the alkaline material providing an active alkaline hair relaxing agent.

2. The composition of claim 1 wherein the oleaginous material is selected from the group consisting of petrolatum, mineral jelly and mineral oil and mixtures thereof containing at least about 50 weight percent of petrolatum.

3. The composition of claim 3 wherein the oleaginous material is a petrolatum-mineral oil mixture containing between about 55 and about 65 weight percent petrolatum and comprises about 25 to about 30 weight percent based on the weight of the composition.

4. The composition of claim 2 wherein the clay gellant is comprised of hectorite modified with a quaternized nitrogen-containing compound containing at least one long chain substituent having about 8 to about 20 carbon atoms on the quaternary nitrogen atom, propylene carbonate and a non-polar organic liquid.

5. The composition of claim 6 wherein the clay gellant is present at about 0.1 to about 2 weight percent and the alkaline material is sodium hydroxide present at about 1 to about 3 weight percent as the sole hair relaxing agent.

6. The composition of claim 2 wherein the alkaline material is an alkaline earth hydroxide present in a sufficient amount to provide a cosmetic cream base convertible for use as a no-lye hair relaxer cream when the composition is admixed with an aqueous activator solution containing the salt of a relatively strong organic base with an anion capable of being precipitated by the ion of the alkaline earth under alkaline conditions.

7. The composition of claim 6 wherein the alkaline material is calcium hydroxide present at about 0.1 to about 10 weight percent prior to admixture and the organic base is guanidine.

8. The no-lye hair relaxer resulting from the admixture of the composition of claim 7 and an activator solution containing a salt of the organic base guanidine.

9. The no-lye hair relaxer of claim 8 wherein the activator solution comprises guanidine carbonate present at about 20 to about 30 weight percent prior to admixture.

10. The no-lye hair relaxer of claim 9 wherein the activator solution further includes a water-soluble polyhydroxy compound having about 3 to about 6 carbon atoms and a thickening agent.

11. The composition of claim 1 wherein the alkaline material is an alkaline earth hydroxide present in a sufficient amount to provide part of the hair relaxing agent when the compositions is converted to a no-lye hair relaxer cream by being admixed with an aqueous activator solution containing the salt of a relatively strong organic base with an anion capable of being precipitated by the ion of the alkaline earth under alkaline conditions.

12. The composition of claim 11 wherein the alkaline material is calcium hydroxide present at about 0.1 to about 7 weight percent prior to admixture and the organic base is guanidine.

13. The no-lye hair relaxer resulting from the admixture of the composition of claim 12 and an activator solution containing a salt of the organic base guanidine.

14. The no-lye hair relaxer of claim 14 wherein the activator solution contains guanidine carbonate present at about 20 to about 30 weight percent prior to admixture.

15. The no-lye hair relaxer of claim 15 wherein the activator solution further includes a water-soluble polyhydroxy compound having 3 to about 6 carbon atoms and a thickening agent.

16. The composition of claim 1 wherein the primary nonionic emulsifier is selected from the class consisting of an emulsifying wax prepared from a mixture comprising lipophilic fatty alcohols having from about 12 to about 24 carbon atoms, and a blend of individual lipophilic fatty alcohols having from about 14 to about 22 carbon atoms.

17. The composition of claim 16 wherein the auxiliary emulsifier includes a hydrophilic nonionic emulsifier selected from the group consisting of polyoxyethylene derivatives of fatty acid esters of sorbitol and sorbitol anhydride; polyethylene glycol esters of fatty acids, polyoxyethylene ethers of fatty alcohols, polyethylene oxide-polypropylene oxide condensates and polyoxyethylene lanolin ethers.

18. The composition of claim 1 wherein the auxiliary emulsifier comprises a hydrophilic nonionic emulsifier that is a polyoxyethylene derivative of lanolin; an anionic emulsifier that is a polyoxyethylene oleyl ether phosphate; and an amphoteric emulsifier that is an alkylamphoglycinate having mono- or di-carboxy groups derived from fatty acids having about 10 to about 22 carbon atoms in the fatty alkyl chain.

19. The composition of claim 18 wherein the amphoteric emulsifier is stearoamphoglycinate.

20. The composition of claim 1 wherein the polymeric quaternary nitrogen conditioning agent is prepared by polymerizing a diallyldimethylammonium salt.

21. The composition of claim 1 wherein the polyhydroxy compound is selected from the group consisting of propylene glycol, glycerin, butylene glycol, hexylene glycol and sorbitol.

22. The cosmetic cream base composition of claim 1 wherein
the oleaginous material comprises a petrolatum-mineral oil mixture containing about 55 to about 65 weight percent petrolatum and is present at about 25 to about 30 weight percent based on the weight of the composition and the lipophilic-modified clay gellant is absent;
the primary nonionic emulsifier comprises an emulsifying wax comprising a mixture of lipophilic fatty alcohols predominantly having from about 14 to about 22 carbon atoms in their fatty chain present at about 6 to about 10 weight percent;
the auxiliary emulsifier comprises polyoxyethylene (75) lanolin present at about 1 to about 3 weight percent; polyoxyethylene (3) ether phosphate present at about 0.1 to about 0.5 weight percent and stearoamphoglycinate present at about 0.2 to about 0.5 weight percent;
the polyhydroxy compound is propylene glycol present at about 3 to about 8 weight percent;
the polymeric conditioning agent, when present, is a homopolymer of diallyldimethylammonium salt and is present at about 0.05 to about 2 weight percent;
the alkaline material is calcium hydroxide present at about 4 to about 7 weight percent, and the total weight of the non-water components and alkaline material together comprising no more than about 50 weight percent, on a dry solids basis, of the total composition.

23. A no-lye hair relaxer cream comprising the cosmetic cream base composition of claim 22 admixed with an aqueous activator solution comprising guanidine carbonate present at about 25 to about 30 weight percent prior to admixture.

24. The no-lye hair relaxer cream of claim 23 wherein the cosmetic cream base composition prior to admixture further contains the lipophilic-modified hectorite clay gellant present in an amount of about 2 weight percent.

25. The no-lye hair relaxer cream of claim 24 wherein the admixture comprises about 3.5 to about 6 parts of the cosmetic cream base with one part of activator.

26. The hair relaxer composition of claim 25 further including cosmetic adjuvants selected from the group consisting of auxiliary emollients, auxiliary thickening agents, perfumes, preservatives, and product colorants present in the cosmetic cream base composition, in the activator, or in both.

27. A no-base, no-lye hair relaxer kit comprising the cosmetic cream base composition of claim 22 in one container and an aqueous activator solution comprising about 25 to about 30 weight percent guanidine carbonate prior to admixture, a polyhydroxy compound having 3 to 6 carbon atoms and a thickening agent in another container.

28. The composition of claim 1 wherein the composition is stable to phase separation for at least about four weeks at ambient temperature and at least about one week at elevated temperature.

29. A method for relaxing hair comprising the steps of:
(a) applying to the hair an effective amount of the hair relaxer cream of claim 5;
(b) smoothing the hair relaxer cream on the hair and leaving the hair relaxer cream on the hair for about 5 to about 10 minutes to allow for adequate softening;
(c) further smoothing the hair to facilitate straightening; and
(d) removing the hair relaxer cream from the hair.

30. A method for relaxing hair comprising the steps of:
(a) applying to the hair an effective amount of the hair relaxer cream of claim 13;
(b) smoothing the hair relaxer cream on the hair and leaving the hair relaxer cream on the hair for about 5 to about 10 minutes to allow for adequate softening;
(c) further smoothing the hair to facilitate straightening; and
(d) removing the hair relaxer cream from the hair.

31. A method for relaxing hair comprising the steps of:
  (a) applying to the hair an effective amount of the composition of claim 1;
  (b) smoothing the composition on the hair and leaving the composition on the hair for about 5 to about 10 minutes to allow for adequate softening;
  (c) further smoothing the hair to facilitate straightening; and
  (d) removing the composition from the hair.

32. A no-base, no-lye hair relaxer kit comprising the composition of claim 11 in one container and an aqueous activator solution comprising about 25 to about 30 weight percent guanidine carbonate prior to admixture, a polyhydroxy compound having 3 to 6 carbon atoms and a thickening agent in another container.

33. A viscous, phase-stable, highly alkaline oil-in-water emulsion cream suitable for use as a cosmetic base for a no-base hair relaxer, the emulsion cream containing a sufficient amount of a non-volatile inorganic alkaline material selected from the group consisting of water-soluble alkali metal hydroxide and alkaline earth hydroxide emulsified therein to both provide a pH of from about 12 to about 14 and part or all of the active hair relaxing agent, the emulsion cream being prepared from an oil phase and a water phase which together contain non-water components, including the alkaline material, at no more than about 50 weight percent of the total weight of the emulsion cream,
  the oil phase consisting essentially of about 15 to about 35 weight percent of a lipophilic oleaginous material including zero to about 2 weight percent of a lipophilic-modified clay gellant, about 3 to about 15 weight percent of a primary nonionic emulsifier comprising a mixture of fatty alcohols having from about 12 to about 24 carbon atoms in their fatty carbon chain and about 0.01 to about 1 weight percent of an auxiliary lipophilic anionic emulsifier;
  the water phase containing, in addition to the alkaline material and water, an auxiliary emulsifier comprising a hydrophilic nonionic emulsifier and an amphoteric or zwitterionic emulsifier, the total amount of auxiliary emulsifier in the emulsion cream, including the anionic emulsifier in the oil phase, being at about 0.05 to about 10 weight percent and about 0.1 to about 10 weight percent of a water-soluble polyhydroxy compound having 3 to about 6 carbon atoms,
  all amounts being calculated on a dry solids basis of the total weight of the emulsion cream, the emulsion cream so formed exhibiting a Brookfield viscosity of at least about 100,000 centipoises at about 25 degrees C. and stability against phase separation on storage aging.

* * * * *

UNITED STATES PATENT AND TRADEMARK OFFICE
CERTIFICATE OF CORRECTION

PATENT NO. : 4,950,485
DATED : August 21, 1990
INVENTOR(S) : Muhammad Akhtar and Florine Newell It is certified that error appears in the above-identified patent and that said Letters Patent is hereby corrected as shown below:

Column 14, line 48, change "525,000 cps. Typically" to --525,000 cps, typically--.

Column 16, line 29, change "reacted" to --reached--.

Column 17, line 12, change "followed applying" to --followed by applying--.

Col., 18, line 27 change "claim 3" to --claim 2--.

Col., 18, line 38 change "claim 6" to --claim 4--.

Col., 19, line 14 change "claim 14" to --claim 13--.

Col., 19, line 18 change "claim 15" to --claim 14--.

Signed and Sealed this

Twenty-ninth Day of December, 1992

*Attest:*

DOUGLAS B. COMER

*Attesting Officer*     Acting Commissioner of Patents and Trademarks